Figure 1:
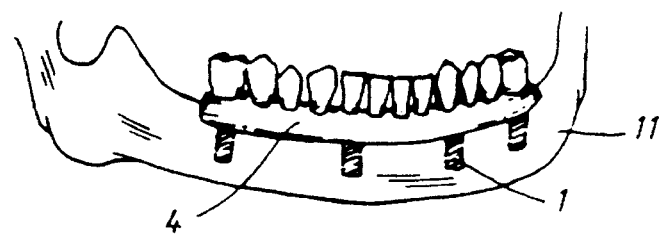

United States Patent [19]

Brånemark

[11] Patent Number: 5,554,027
[45] Date of Patent: Sep. 10, 1996

[54] PROSTHESIS SYSTEM FOR REPLACING TEETH

[75] Inventor: Per-Ingvar Brånemark, Molndal, Sweden

[73] Assignee: Medevelop AB, Sweden

[21] Appl. No.: 234,052

[22] Filed: Apr. 28, 1994

[30] Foreign Application Priority Data

Apr. 28, 1993 [SE] Sweden ................... 9301424

[51] Int. Cl.$^6$ .................................. A61C 13/22
[52] U.S. Cl. .................... 433/172; 433/169; 433/173
[58] Field of Search ..................... 433/169, 168.1, 433/172, 173

[56] References Cited

U.S. PATENT DOCUMENTS

| | | |
|---|---|---|
| 3,866,321 | 2/1975 | Valen . |
| 4,713,003 | 12/1987 | Symington et al. ............ 433/173 |
| 4,904,186 | 2/1990 | Mays ............................... 433/172 |
| 4,931,016 | 6/1990 | Sillard ............................. 433/172 |
| 5,057,017 | 10/1991 | Sillard ............................. 433/172 |

FOREIGN PATENT DOCUMENTS

| | | |
|---|---|---|
| 8306535 | 9/1986 | Sweden . |
| 8503580 | 3/1987 | Sweden . |
| 8502337 | 6/1985 | WIPO . |

*Primary Examiner*—Cary E. O'Connor
*Attorney, Agent, or Firm*—Ostrolenk, Faber, Gerb & Soffen, LLP

[57] ABSTRACT

A prosthesis system for replacing two or more adjacent teeth comprises prefabricated elements for fixing to the lower or upper jaw of a patient. The prefabricated elements include an arcuate bridge base, two or more substantially rotationally symmetric spacer elements, and, for each spacer element, a respective fixture or screw implantable in the jawbone. The system further includes an arcuate dental bridge comprising teeth, and an arcuate profile element supporting the teeth. On its underside the profile element has a groove or channel to receive the bridge base. Each implantable fixture or screw has a screw-threaded bore extending from its outer end for reception of a corresponding screw-threaded shank at one end of the respective spacer element. The bridge base has bores therein to receive fitting portions of the spacer elements and the bridge base is secured to the spacer elements by adhesive and/or by securing screws or nuts. Screws extending through transverse bores in the base and the side walls of the profile element secure the dental bridge to the bridge base. The prosthesis is provided with damping between the bridge and the bridge base.

20 Claims, 2 Drawing Sheets

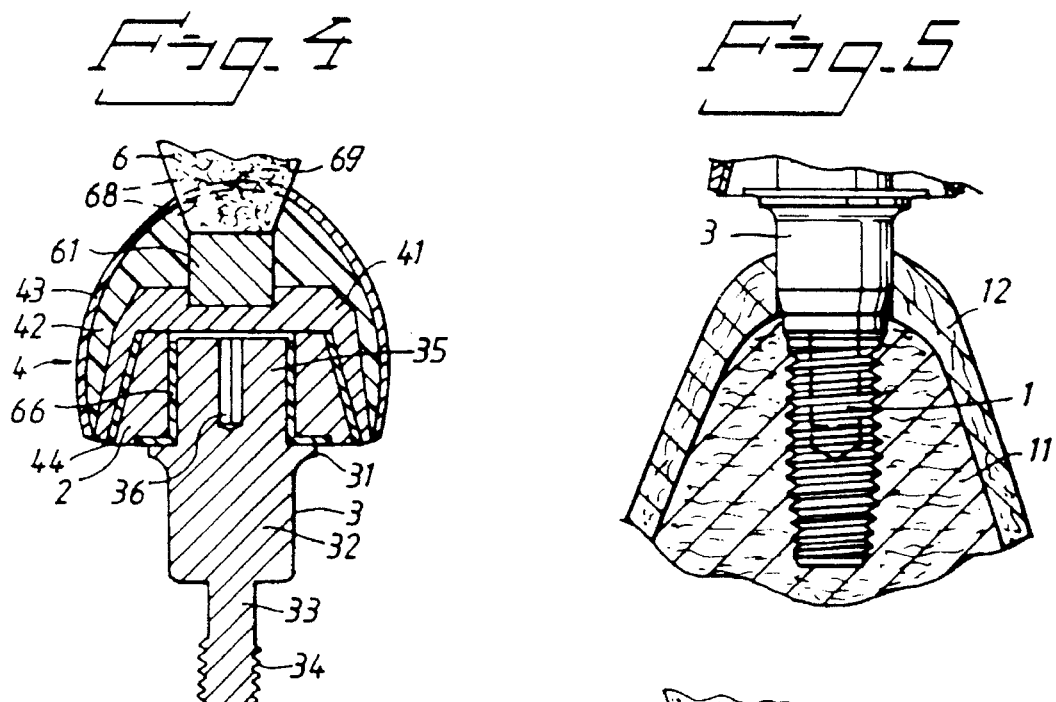
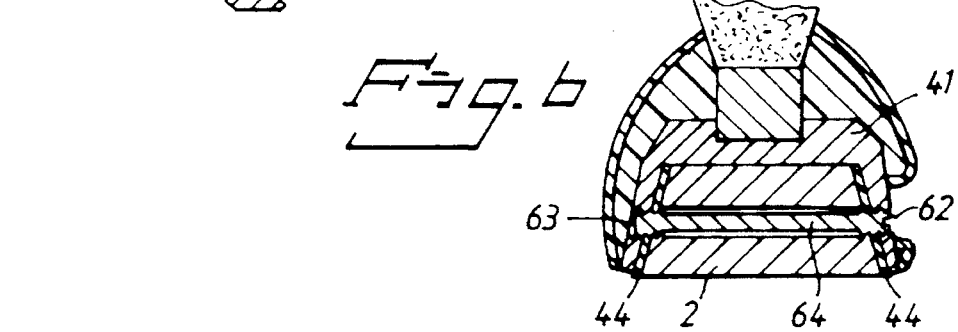
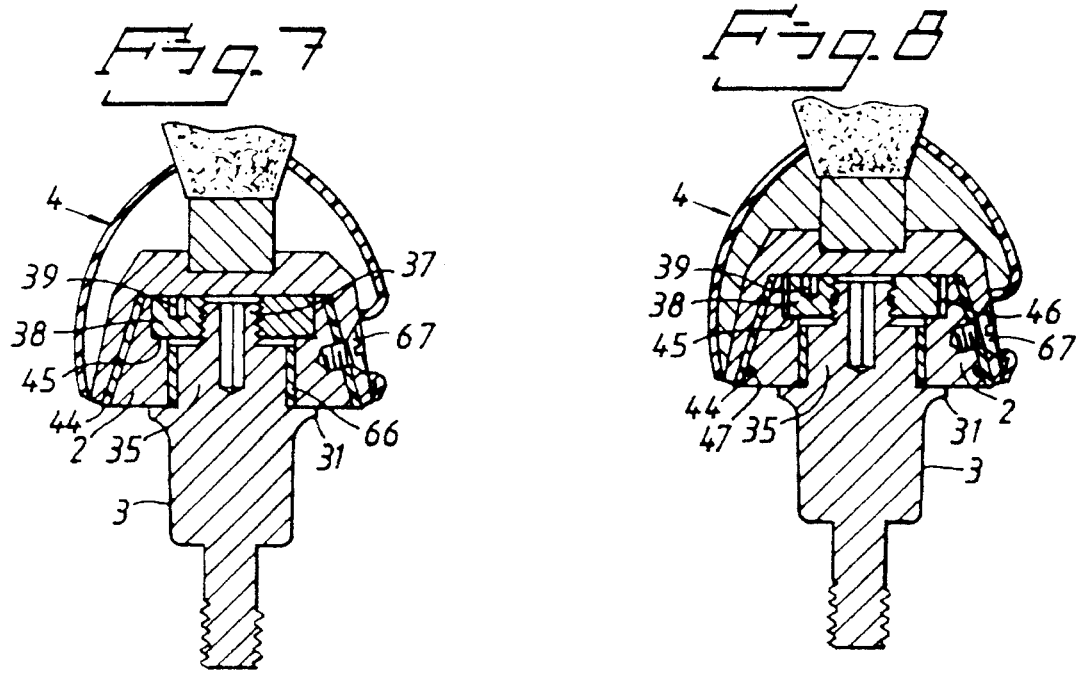

PROSTHESIS SYSTEM FOR REPLACING TEETH

The present invention relates to a prosthesis system for replacing prosthetically two or more adjacent teeth in the upper or lower jaw of a patient, the system utilising prefabricated elements intended for fixing to the lower or upper jaw.

The invention also relates to a method of replacing teeth prosthetically using the system.

It is known to replace missing teeth prosthetically in patients by a technique in which fixtures are implanted in the jawbone or the bone of the upper jaw. In order to make the anchoring of the fixtures permanent a number of requirements have to be met, i.e. factors connected with selection of materials and surgical technique. In practical use the fixtures in the form of screws of pure titanium developed by Prof. Branemark have shown very good long-term anchoring properties. The fixture screws are anchored in the jawbone by surgery and permitted to become integrated with bone tissue—osseointegrated—by a healing process extering over a certain period of time, several months in general. Thereupon teeth can be mounted on the fixtures.

In published Swedish Patent Application No. 448,599 (Application No. 8503580-6) there is disclosed an arrangement for securing a row of teeth to at least two fixtures implanted into the jawbone, the arrangement comprising a stiff bar of titanium fixed to the fixtures and mounting means for releasably fixing the row of teeth on the bar. Between the row of teeth and the bar elastic damping means are arranged.

Published Swedish Patent Application No. 446,370 (Application No. 8306535-9) discloses the use of a spacer element also in the form of a screw which, at its one end, has external threads for fixing in a screw threaded bore of a fixture of the type referred to above. At its other end, the spacer element is conically tapering for cooperation with a sleeve formed like the frustum of a cone arranged between the spacer element and the dental prosthesis, said sleeve having a bottom provided with a central hole from which the sleeve widens. The dental prosthesis is fixed to the spacer element mounted in the fixture by means of a screw or similar fixing means connecting the dental prosthesis and the spacer element and extending through a hole in the bottom of the cone-shaped sleeve.

The mounting of dental bridges requires much effort, this being the reason for costs for reconstruction of entire upper and lower jaws being relatively high. In addition, for each patient, the total time needed for reconstruction is prolonged. Therefore it is desirable to reduce costs for reconstruction of entire jaws— or for prosthetically reconstructing a continuous part of a row of teeth— by application of user-friendly solutions aiming at a reduction of time and work for implantation and mounting.

It is an object of the present invention to provide a prosthesis system for replacing a plurality of adjacent teeth and a method for anchoring of the system in the jaw of a patient by means of which the time and work required for implantation and rehabilitation can be substantially reduced as compared with what is known, and which also possesses other valuable and surprising features.

According to the invention, there is provided a prosthesis system for replacement of missing teeth based on prefabricated elements intended for fixing to the lower or upper jaw, the system comprising an arcuate bridge base, two or more substantially rotationally symmetric fixtures implantable in the bone of the lower or upper jaw of a patient, respective rotationally symmetric spacer elements for said fixtures, an arcuate dental bridge comprising (a) teeth, and (b) an arcuate profile element supporting the teeth, said profile element being adapted for abutting engagement with the bridge base, means for fixing the bridge base to the spacer elements, and means for fixing the dental bridge to the bridge base, the last-mentioned means for fixing comprising fixation means arranged on or in the profile element.

The arrangement of a bridge base entirely separate from the dental bridge proper provides, as will be evident from the following, major advantages in respect of, for example, constructional flexibility of the prosthesis, adaptation to the patient, mounting, and load strength properties.

Preferably the profile element is of channel section providing a longitudinally extending groove to receive the bridge base, the artificial teeth being mounted on the opposite side of the base from the side on which the channel side walls extend. The side walls of the channel preferably diverge away from the bone for abutment against the correspondingly diverging side surfaces of the bridge base. This kind of profile provides for exact positioning and reduces load on the fixing means fixing the profile element to the base.

It is preferred for the fixing means securing the dental bridge on the bridge base to have substantially horizontal extension. This has the advantage that these fixing means can easily be hidden which is desirable from an aesthetic standpoint.

It is also preferred for the bridge base to be provided on its underside with a cylindrical bore for each spacer element, each said bore being arranged to receive a cylindrically formed fitting section of the spacer means.

It is furthermore preferred for the fitting section of the spacer element to extend from support means for support of the bridge element in the direction of the upper end of the spacer element (i.e. the end remote from the respective fixture). At its lower end the spacer element is provided with an external thread for screw-threaded engagement in a screw-threaded bore of the fixture.

According to another aspect of the invention the dental bridge, on its side facing away from the base on which it is mounted, is at least partially clad with plastics material comprising a flexible outer layer surrounding an elastically compressible inner layer. The outer layer is preferably fixed at the lower front and rear edges of the profile element and the tooth bases. This supplements the advantages properties of the prosthesis with a "natural feel".

According to a third aspect of the invention the means for fixing the bridge base to the spacer elements comprises agents forming hard layers selected from the group rapidly setting compositions, particularly hardenable isocyanates and polyurethane, and porcelain cement, screw means, or their combinations. Thereby the prosthesis can also be adapted to fixtures less than exactly positionally fixed in the jawbone.

It is also preferred for the means for fixing the dental bridge to the bridge base to comprise screw means extending through holes in the bridge base and releasably fixed in the profile element; this facilitates mounting and temporary removal for adjustment of the prosthesis.

To reduce the effect of chewing and biting forces on the anchorage in the bone it is advantageous to arrange damping means between the dental bridge and the bridge base. The damping means preferably comprises polymeric material.

For prevention of penetration of humidity inbetween the bridge base and the dental bridge (possibly resulting in colonization of these parts by micro-organisms) sealing means are arranged between the dental bridge and the bridge base. By appropriate choice of material and design the sealing means can also be comprised by the damping means.

The prosthesis system according to the invention is intended for use in replacement of teeth lost due to various factors, such as by physical accident, surgical extraction or by periodontitis.

The invention also relates to a method of prosthetically replacing teeth in a patient, more particularly replacing two or more adjacent teeth arranged in the upper jaw or lower jaw of a patient. The inventive method comprises implantation into the jawbone of two or more substantially cylindrical fixtures, fixation of a respective spacer element each at the free end of each fixture, optionally directly after operation or after the fixtures have become integrated with bone tissue during a healing phase and have become optimally anchored, fixing a bridge base on the spacer elements, and fixing a dental bridge on the bridge base. It is preferred for the method according to the invention to comprise temporary fixing of a gum bridge on the bridge base. It is advantageous to use a drilling jig when drilling the holes for the fixtures in the bone. The drilling jig has guides arranged in correspondence to the holes in the base bridge intended for reception of the spacer elements.

In the following, embodiments of the invention are described in more detail with reference to the accompanying drawings illustrating a preferred but not limiting embodiment of a prosthesis system embodying the invention attached to a lower jaw by four fixtures.

IN THE DRAWINGS

Figure 2:
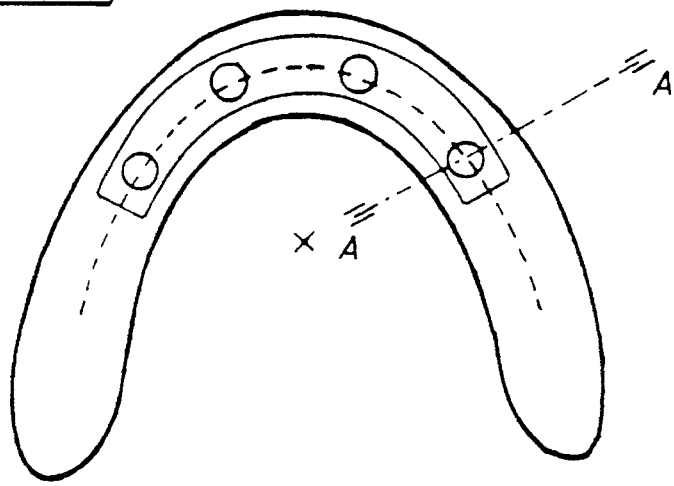
Figure 3:
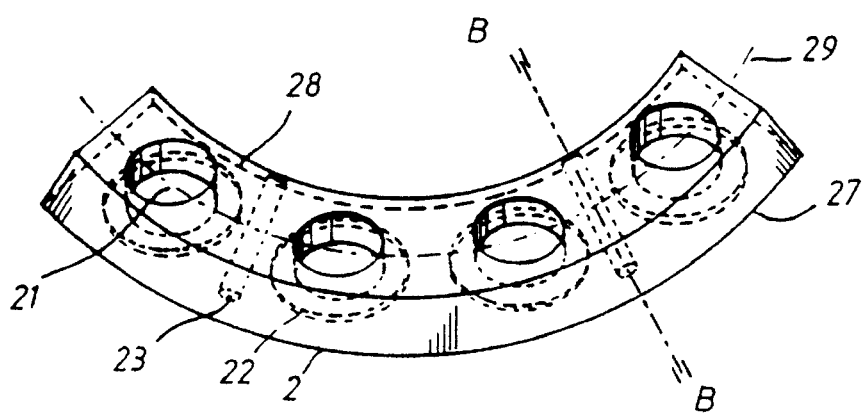

FIG. 1 is a perspective oblique front view of a patient's jaw bone, illustrating the principle of location of a prosthesis system embodying the invention in the lower jaw, FIG. 2 is a plan view corresponding to FIG. 1, but with a dental bridge and teeth of the prosthesis system omitted to show a base plate, FIG. 3 is a perspective view showing the bridge base of FIG. 2, FIG. 4 shows the prosthesis system of FIG. 1, in a vertical section along the line A—A of FIG. 2, with the jawbone and fixing screws omitted, FIG. 5 is a partial, only partially sectioned view along the line A—A of FIG. 2 showing the jawbone, fixing screw and a spacer secured to the fixing screw, but showing only a minor part of the remainder of the prosthesis system, FIG. 6 is a view of the prosthesis system of FIG. 1, in a vertical section along line B—B of FIG. 3 and omitting the jawbone, fixing screws and other parts, FIG. 7 is a view similar to FIG. 4 but showing a variant prosthesis system, and FIG. 8 is a view similar to FIGS. 7 and 4, showing another variant of the prosthesis system.

The prosthesis system shown in FIG. 1 is fixed to the lower jaw of a patient by means of four fixtures 1 and comprises, in addition to the fixtures 1, a bridge base 2 not visible in FIG. 1, a dental bridge 4, partially surrounding the bridge base 2, and four spacer elements 3 which likewise are not visible in FIG. 1.

The fixtures 1 are of known design and are only superficially illustrated in FIG. 5. They have substantially cylindrical form and are externally screw threaded for screwing into pre-drilled and, possibly prescrew-threaded, bores in the jawbone 11. The fixtures 1 are screwed into the jawbone 11 to such a depth that their free, upper ends are located in the border zone between the jawbone 11 and the soft tissue 12 of the gum, as shown in FIG. 5. The free ends of fixture screws 1 have screw-threaded bores for mounting of the prosthesis itself which may be a tooth of a dental bridge. In the illustrated embodiment the mounting of the bridge 4 is accomplished by the four spacer elements 3 each fixed to the upper end of a respective fixing screw 1 by means of an integral externally screw-threaded shank 33 of the respective spacer element 3 being screwed into the screw threaded bore in the respective screw 1. In FIG. 4 the screw thread on the lower shank portion 33 of the spacer element 3 is referenced by numeral designations 34. At its upper end, the shank portion 33 meets a body 32 of the spacer, providing an annular shoulder designed for optimal fit against the free upper end face of the respective fixing screw 1.

The spacer element 3 of titanium is rotationally symmetric and consists of said cylindrical body 32 with a fitting end portion 35 at its upper end separated from the body 32 by a circumferential annular flange 31 radiused in the region where it is joined to the body. A hexagonal socket 36 extends axially into the spacer element from the upper end of the fitting end portion 35 and is intended to receive a driving tool or key of complementary hexagonal section for mounting the spacer element 3 on the fixture 1.

As is evident from FIGS. 3 and 4, the bridge base 2, which is of titanium, has an arcuate shape and is of trapezoid cross section. Its arcuate shape is intended to be mounted by means of the fixtures 1 and the spacer elements 3. The bridge base 2 is provided with four substantially equidistant holes 21 arranged along its longitudinal extension, each hole 21 passing through base 2 from the upper side of the bridge base to its underside. A respective shallow annular ring-formed recess 22 is milled in the underside of the bridge base 2, concentric with each hole 21, as shown in broken lines in FIG. 3, the radius of each said recess 22 being somewhat larger than the radius of the flange 31 on each spacer element 3. Two bores 23 each arranged between the holes 21 of a respective pair of holes 21 extend through the bridge base 2 from its front side to its rear side (facing the tongue), said bores 23 extending substantially radially and parallel to the upper and lower surfaces of the bridge base.

The dental bridge construction 4 includes a titanium element 41 which is in the form of an inverted, generally U-section channel with side walls diverging away from the channel "base". The element 4 has essentially the same longitudinal extension as the bridge element 2. The channel defined by profile element 41 thus has a generally trapezoidal cross section which is congruent in shape with the outside of the bridge base 2 (i.e. with the top, front and back of the base 2) and is thus capable of fitting closely over base 2. Artificial teeth 6 are fastened on top of the element 41 at intervals therealong, said teeth imitating, in respect of their number, size mutual spacing and appearance, the teeth to be replaced by the prosthesis system. The teeth 6 are fastened in the profile element 41 by means of holding means 61 not shown in greater detail. In its rear wall, the profile element 41 has two bores 62 (FIG. 6) and in its front wall the element 41 has two bores 63 each aligned with a respective bore 62. The arrangement is such that, after the profile element 41 has been positioned on the bridge base 2, each pair of bores 62, 63 is aligned with a respective bore 23 in base 2, (cf. FIG. 3). The bores 62, 63 are screw threaded.

The surfaces of the profile element 41 which face away from the inverted channel are clad with a composite polymer material which, as much as possible, imitates the gum in respect of form, look and feel. The composite material consists of a comparatively soft, compressible inner layer 42 of urethane polymer with closed gas-filled cells, and a harder, flexible compact outer layer 43 of polyurethane. The layers 42 and 43 are glued to the profile element 41 and around the bases of teeth 6 by a setting adhesive based on isocyanates. A damping layer 44 is provided between the bridge base 2 and the profile element 41. The damping layer 44 may comprise a polymer. More particularly, the damping layer 44 may comprise polyurethane.

The dental bridge is mounted on the bridge base 2 by means of two screws 64. Each screw 64 is screwed through the hole 62 in the rear wall of the profile element 41, then is passed through the hole 23 in the bridge base 2 located in line with that hole 62 and thereupon is screwed into the hole 63 in the front wall of the profile element 41. The areas around holes 62 in the rear wall of element 41 are not covered by composite polymer material. The damping polyurethane layer 44 also has holes for passage of the screws 64.

The bridge base is glued or cemented onto the spacer elements 3 by means of, for instance, a polyurethane-based setting adhesive or a rapid hardening porcelain cement indicated at 66 in FIG. 4. There is sufficient clearance between the bridge base 2 and the spacer elements to permit fine adjustment of the position of base 2 relative to spacer elements 3 and to receive the glue or cement 66.

Two variants of the embodiment described in the foregoing are shown in FIGS. 7 and 8. These Figures show different ways of securing the bridge base on the spacer elements 3. In both cases the fitting end portion 35 of the spacer element 3 has an externally threaded cylindrical end section 37 (FIG. 7) of reduced diameter and an annular nut 38 is screwed onto the screw-threaded end section 37. The nut 38 is provided with three engagement holes 39 for engagement by a driving tool or key for screwing the nut 38 onto section 37 or unscrewing the nut 38. In its secured state, nut 38 abuts an upwardly facing annular step 45 at the end of a counterbore formed in the hole 21 of the bridge base 2. Thus, the bridge base 2 is clamped between the annular flange 31 of the spacer element 3 and the nut 38 so that vertical play of the base 2 relative to spacer elements 3 is eliminated.

In the variant according to FIG. 7 horizontal play is also eliminated since the outer diameter of each annular nut 38 corresponds to the diameter of the respective counterbore providing the respective annular step 45. In the variant according to FIG. 8 horizontal play is still possible since the outer diameter of each annular nut 38 is smaller than the diameter of the counterbore providing the respective step 45, and at the same time the outer diameter of the fitting portion 35 of each spacer element 3 is smaller than the part of the hole 21 in the bridge base 2 which receives it. Lateral displacement of the base 2 relative to screws 3 during long-term use can be prevented by filling the clearances between bores 21 and spacers 3 with cement or a polymer, said cement or polymer hardening after positional fixation has been obtained by tightening annular nut 38.

To prevent moisture penetrating between the bridge base 2 and the bridge 4 in the variant according to FIG. 8, a sealing strip 47 is arranged in a groove extending along the lower front edge of the base element 2. The damping layer 44 can also have a sealing function. In the variants according to FIGS. 7 and 8 the dental bridge 6 is fixed on the bridge base 2 by means of screws 67 which do not pass completely through the bridge base 2.

It will be appreciated that, in the embodiment of FIG. 4, since location of the base 2 on the spacers 3 is by adhesive or cement only it is not strictly necessary for the bores 21 to pass completely through the base 2. Thus, in a variant, not shown, the bores 21 may be blind bores extending from the underside of the base 2.

For the parts of the system bordering living tissue only epidermally or not at all various types of corrosion-resistant materials can be used, such as steel alloys or ceramic materials. The risk of formation of galvanic currents must, however, be taken account of where a combination of different metals is used.

Any of the prosthetic systems described above with reference to the drawings is implanted by surgery and mounted in the following way. A bridge base 2 fitting the jaw 11 of the patient is manufactured or selected from a set of standard size bridge bases 2. Four vertical holes are drilled into the jawbone at positions and mutual spacings corresponding to those of the holes 21 in the bridge base 2. The accuracy of such drilling can be increased by preparing a drilling jig with a bore guide arrangement corresponding to the position and relative distances of holes 21 in the bridge base 2. The fixtures 1 are anchored by surgery, that is, are screwed carefully into the holes provided in the jawbone 11, possibly after providing threads in the holes. Alternatively the fixtures 1 may be self-tapping.

During a healing phase which may have a duration of several weeks to several months the fixtures 1 should not be put under appreciable load, such as a load caused by chewing. The healing attachment can be accomplished in the traditional way, that is, by closing the outer ends of the fixtures by screws fitting into the inner threads and folding back the dissected skin flap which is allowed to become attached by healing. Some months later the skin is again opened and the screws over the fixtures 1 are removed. The spacer elements 3 can now be mounted in the fixtures 1.

It is, however, extremely advantageous for the implantation of the fixtures 1 and the mounting, including positional fixation of the bridge base 2, to be carried out in a single step. The design of the components in the present system supports such a one-session method. In this method the spacer elements 3 are mounted on the fixtures 1 and the bridge base 2 is mounted on the spacer elements directly after the operation. The positional fixation of the bridge base 2 depends on the chosen variety of bridge base 2 as described above. In cases where only hardenable polymers or cement are used to fix the base 2 relative to spacers 3, as is the case, for example, with the embodiment according to FIGS. 1–6, satisfactory hardening of the polymers or cement has to be awaited before the next steps in the method can proceed. After such hardening, a temporary bridge is mounted, that is, a bridge 4 which is lacking teeth 6 and which cannot be used for chewing. The cross-sectional contour of such a temporary bridge is, as indicated in FIG. 4 the same as that of the bridge 4 of FIG. 4, except, of course, for the regions of the teeth, where the profile 68 is as indicated in broken lines in FIG. 4. The temporary bridge can be worn by the patient during the healing stage, that is, for some weeks to some months after operation. In some isolated cases the permanent dental bridge may be mounted directly, there being no need for prior mounting of a temporary bridge. The kind of measures taken must, of course, be dependent on medical judgement of the individual case.

A considerable advantage with the present system is that the dental bridge 4 can be easily removed for inspection and, possibly, be temporarily substituted by a provisional or temporary bridge. Another advantage of the system is that it makes it possible to cater for the major part of the patient population with a limited assortment of bridge bases 2 and accompanying dental bridges 4, both possibly as semi-finished products or blanks. When designing a standardized assortment of bridges, variations in the following parameters must be provided for, referring to FIGS. 3 and 4; the curvature of the lower front edge 27 of the bridge base (approximately the major radius of the bridge base); the curvature of the lower inner edge 28 of the bridge base 2 (approximately the minor radius of the bridge base); and the curvature of the curve 29 drawn through the centres of holes 21 in the bridge base. In addition it is appropriate to use the distance between the underside of the bridge base 2 and the apex 69 of the artificial gum 42, 43 of the bridge 4 or between the underside of the bridge base 2 and the top side or any other suitable height parameter as well as the length of the bridge base 2. Standardized bridge bases 2 can be provided with holes 21 and all other accompanying elements such as threads and abutment shoulders, but these advantageously can also be added locally by the dental surgeon or dental mechanic for optimal adaptation to the individual patient.

An assortment of components for the prosthesis system according to the invention also can comprise blanks for bridge bases, which blanks lack the bores necessary for attachment of spacer elements 3. These blanks may be provided with such holes or bores after the prosthesis has been adapted to the patient; this allows even better adaptation to the needs of the individual patient. For similar reasons it can be advantageous for the assortment to include also blanks for dental bridges having at least profile elements 41; these blanks also are finished, for example by the dental technician providing them with teeth, according to the requirements of the treatment of the individual patient.

In the variants according to FIGS. 7 and 8 it is possible advantageously to provide means for the adaptation of the heights or the effective heights of the spacer elements 3. This can be accomplished, in the most simple manner, by an assortment of annular inserts or washers (not shown) which can be placed on the shoulders 31 of the spacer elements 3 before applying the base 2, but also other methods are conceivable, such as, for instance, varying the depth to which the spacer elements 3 are screwed into the fixtures 1.

It will be appreciated that, whilst, for ease of description, the prosthesis systems described with reference to the drawings have been described as being fitted to the lower jaw of a patient, the systems described can just as readily be fitted to the upper jaw of a patient. The system will then be inverted as compared with the orientation shown in the accompanying drawings and the references in the foregoing description to "top", "upper ends", etc. should be understood as references to "bottom", "lower ends", etc. in relation to such an inverted mounting.

I claim:

1. A prosthesis system for replacement of missing teeth, the system comprising: an arcuate bridge base, two or more substantially rotationally symmetric fixtures implantable in the bone of the lower or upper jaw of a patient, respective rotationally symmetric spacer elements for said fixtures, an arcuate dental bridge, said bridge including teeth and an arcuate profile element supporting the teeth, said profile element being adapted for abutting engagement with the bridge base, said bridge base being a prefabricated element requiring no individual adaptation to accommodate the jaw of the patient, the system including means fixing the bridge base to the spacer elements, and means arranged on or in the profile element for fixing the dental bridge to the bridge base.

2. The prosthesis system of claim 1, in which the profile element has the form of a channel section element having a base from which said teeth extend and side walls extending from said base in the opposite direction from said teeth, said channel section element providing a longitudinally extending groove or channel for receiving the bridge base.

3. The prosthesis system of claim 2, in which the side walls of said channel section diverge in a direction away from the teeth.

4. The prosthesis system of claim 1 in which the fixing means for fixing the dental bridge on the bridge base extend in a direction transverse to the direction in which said teeth extend from said profile element.

5. The prosthesis system of claim 1 in which the bridge base is provided, on its underside, with a respective cylindrical bore for each spacer element, arranged to receive a cylindrical fitting section of the spacer element.

6. The prosthesis system of claim 5, in which, in each said spacer element, integral support means for support of the bridge base is provided on the periphery of the spacer element, intermediate its ends, and in which the fitting section of each spacer element extends from said support means of the element.

7. The prosthesis system of claim 1, wherein each said fixture has an insertion end for insertion in a bore in the bone of a patients jaw and has a screw-threaded bore extending from its opposite end and wherein each said spacer element has, at one end, a shank provided with an external thread for screw-threaded engagement in the screw-threaded bore in a said fixture.

8. The prosthesis system of claim 1, in which the dental bridge on its side facing away from said base, is at least partially clad with plastic material comprising a flexible outer layer surrounding an elastically compressible inner layer.

9. The prosthesis system of claim 8, in which the outer layer is fixed to the surfaces of the profile element facing away from said base.

10. The prosthesis system of claim 1, in which the bridge base is fixed to the spacer elements by a rapidly hardenable cement.

11. The prosthesis system of claim 10, wherein said cement is selected from the group comprising hardenable isocyanates and polyurethanes, and porcelain cement.

12. The prosthesis system of claim 1, in which the bridge base is fixed to the spacer elements by screw means.

13. The prosthesis system of claim 1, in which the means for fixing the bridge to the bridge base comprise screw means extending through holes in the bridge base and into the profile element.

14. The prosthesis system of claim 1, in which damping means are arranged between the dental bridge and the bridge base.

15. The prosthesis system of any of claim 1, in which sealing means are arranged between the dental bridge and the bridge base.

16. The prosthesis system of claim 15, in which the sealing means also forms damping means operative between said insert and said base.

17. Use of the prosthesis system according to claim 1 for replacing missing teeth.

18. A method of replacing prosthetically two or more adjacent teeth in the upper jaw or lower jaw of a patient, the method comprising:

implanting into the bone of the upper or lower jaw two or more substantially cylindrical fixtures, fixing a respective spacer element at the free end of each said fixture, providing a prefabricated bridge base requiring no individual adaptation to accommodate the jaw of the patient, fixing said prefabricated bridge base on the spacer element, and fixing a dental bridge on the prefabricated bridge base.

19. The method of claim 18, which also comprises the step of fixing a temporary toothless bridge on the bridge base and retaining said temporary bridge in place during a healing phase, and subsequently removing the temporary bridge before fitting said dental bridge on the bridge base.

20. The method of claim 19, in which a drilling jig is used in drilling holes in said bone to receive said fixtures.

* * * * *